United States Patent
Milo et al.

(10) Patent No.: US 8,455,019 B2
(45) Date of Patent: Jun. 4, 2013

(54) FOOD OR BEVERAGE COMPOSITION COMPRISING UNROASTED COFFEE SOLIDS

(75) Inventors: Christian Milo, Dublin, OH (US);
Francois Vandon, Lausanne (CH);
Ching-Jung Kuo, Marysville, OH (US);
Aneola Kamal, Chardonne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/266,700

(22) PCT Filed: Apr. 15, 2010

(86) PCT No.: PCT/EP2010/054941
§ 371 (c)(1),
(2), (4) Date: Oct. 27, 2011

(87) PCT Pub. No.: WO2010/124936
PCT Pub. Date: Nov. 4, 2010

(65) Prior Publication Data
US 2012/0040027 A1    Feb. 16, 2012

Related U.S. Application Data

(60) Provisional application No. 61/173,270, filed on Apr. 28, 2009, provisional application No. 61/220,665, filed on Jun. 26, 2009.

(51) Int. Cl.
*A01N 65/00* (2009.01)

(52) U.S. Cl.
USPC .................................................. 424/725

(58) Field of Classification Search
None
See application file for complete search history.

(56) References Cited

U.S. PATENT DOCUMENTS

| | | |
|---|---|---|
| 2,758,927 A | 2/1953 | Chase |
| 5,972,409 A | 10/1999 | Liu et al. |
| 2009/0010904 A1 | 1/2009 | Iwai et al. |

FOREIGN PATENT DOCUMENTS

| | | |
|---|---|---|
| EP | 1600461 | 11/2005 |
| EP | 1674106 | 6/2006 |
| FR | 2734479 | 11/1996 |
| WO | 2006108578 | 10/2006 |

OTHER PUBLICATIONS

PCT International Search Report for Application No. PCT/EP2010/054941 with a Mailing Date of Jun. 30, 2010. 2 Pages.

*Primary Examiner* — Michael Meller
(74) *Attorney, Agent, or Firm* — K&L Gates LLP

(57) ABSTRACT

The present invention relates to a food or beverage composition comprising unroasted coffee solids and arabinogalactans, for example a ready-to-drink beverage.

1 Claim, No Drawings

FOOD OR BEVERAGE COMPOSITION COMPRISING UNROASTED COFFEE SOLIDS

CROSS REFERENCE TO RELATED APPLICATIONS

The present application is a National Stage of International Application No. PCT/EP2010/054941, filed on Apr. 15, 2010, which claims priority to U.S. Pat. No. 61/173,270 filed Apr. 28, 2009 and U.S. Patent Application No. 61/220,665 filed on Jun. 26, 2009, the entire contents of which are being incorporated herein by reference.

FIELD OF THE INVENTION

The present invention relates to a food or beverage composition comprising unroasted coffee solids.

BACKGROUND

Coffee contains antioxidants that are thought to have beneficial effects on the health of human beings or animals consuming it. Traditionally, coffee is consumed as a water extract of roasted coffee beans. It is however known that the amount of antioxidants is reduced by the roasting process, therefore there has been interest in using the green, unroasted coffee beans to increase antioxidant content of coffee products and for use as an ingredient in other food products. The green coffee beans do not have the typical flavour of coffee and consequently extracts of green coffee have only been used in low concentrations in foods and beverages. Coffee beans also comprise arabinogalactans which may have positive health effects such as prebiotic and immunostimulatory effects and positively influence gut health and digestion in humans and animals.

U.S. Pat. No. 2,758,927 discloses extraction of green coffee beans with water, the dried green coffee extract is subsequently subjected to a roasting process to produce the typical roasted coffee aroma. WO 2006/108578 to Nestec SA discloses a process wherein both roasted and green coffee beans are extracted to yield a product high in antioxidant content but with a taste and aroma including the typical aroma of roasted coffee. FR 2734479 to Berkem SA and EP 1674106 to Oryza Oil & Fat Chemical Company Ltd. both disclose processes for extraction of green coffee beans wherein organic solvents are used to obtain an extract enriched in bioactive components without the typical aroma of coffee.

There is a need for food and beverage products comprising unroasted coffee solids having a pleasant taste and aroma and delivering the beneficial effects associated with green coffee, especially a food or beverage product with a refreshing, yet coffee-like, character.

SUMMARY OF THE INVENTION

The inventors have now found that a food or beverage composition comprising unroasted coffee solids and arabinogalactan has a pleasant refreshing taste and aroma, accordingly the invention relates to a food or beverage composition comprising at least 0.1% coffee solids and at least 20 milligram of arabinogalactan per gram of coffee solids, wherein at least 80% of said coffee solids are water soluble, and at least 92% of said coffee solids are unroasted coffee solids.

DETAILED DESCRIPTION OF THE INVENTION

Coffee Solids

Coffee solids according to the invention are any compounds derived from coffee, excluding water. Coffee solids according to the invention are preferably derived from coffee beans. The composition of the invention comprises at least 0.1% (by weight) coffee solids, such as at least 0.2%, 0.3% or at least 0.4% coffee solids. In one embodiment of the invention, the composition of the invention comprises up to 20% coffee solids, such as up to 10% or up to 5% coffee solids, e.g. between 0.1% and 20%, between 0.2% and 10%, or between 0.2% and 5% coffee solids. The coffee solids of the composition of the invention are preferably water soluble. By water soluble is meant soluble in water at 90° C. According to the invention at least 80% (by weight) of the coffee solids of the composition of the invention are water soluble, such as at least 90% or at least 95%. Water soluble coffee solids may e.g. be obtained by extraction of coffee beans with water.

At least 92% of the coffee solids of the composition of the invention are unroasted coffee solids. In one embodiment at least 95%, such as at least 98%, of the coffee solids of the composition of the invention are unroasted coffee solids. In one embodiment of the invention all the coffee solids of the composition are unroasted coffee solids. By unroasted coffee solids are meant coffee solids that have not been subjected to a roasting process. Roasting of coffee solids are normally performed on the raw green coffee beans before grinding and extraction of the beans, but may also be performed on the ground beans or on an extract of soluble coffee solids that has been dried. By roasting is meant a heat treatment of the dry, or almost dry, coffee solids as opposed to e.g. cooking of coffee solids in water, e.g. under pressure. Roasting is thus different from the heat treatment in water which may take place during extraction of coffee at elevated temperatures. The purpose of roasting of coffee is usually to develop the specific flavour notes characteristic of roasted coffee. In one embodiment of the invention, unroasted coffee solids are coffee solids that have not been subjected to heat treatment at a temperature above 100° C. at a moisture level below 30% (by weight), preferably below 20%. The moisture level is understood as the proportion of water contained in the coffee solids composition, e.g. coffee beans or dried coffee extract, or in a mixture of the coffee solids with water, e.g. a mixture of whole coffee beans with water, a slurry of ground coffee beans in water, or a coffee extract dissolved in water.

The coffee solids of the composition of the invention may be obtained by any suitable method. In a preferred embodiment coffee solids originate from extraction of raw, also called green, coffee beans. The green coffee beans may be whole or ground when extracted. The green coffee beans are preferably extracted with water, preferably without addition of any organic solvent. Green coffee beans may be extracted with water in any suitable manner. Methods for water extraction of green and/or roasted coffee beans are well known in the art. E.g. U.S. Pat. No. 5,972,409, which is incorporated herein by reference, discloses suitable methods for extraction of green coffee beans. The proportion of arabinogalactan extracted from the coffee beans increases with temperature. To extract the required proportion of the arabinogalactan, green coffee beans are preferably extracted with water at a temperature above 130° C., such as above 140° C., or above 150° C. Extraction may be performed in one or more stages at different temperatures, e.g. a first stage at less than 120° C. and a second stage at above 140° C.

Arabinogalactan

Arabinogalactan is a family of polysaccharides (proteoglycans) implicated in plant growth and development. The major part of arabinogalactan consists of polysaccharide, composed mainly of b-(1-3)galactan chains with b-(1-6)-galactosyl side chains terminated primarily with arabinosyl residues. The composition of the invention comprises at least 20 mg of arabinogalactan per g of coffee solids. In one embodiment the composition of the invention comprises at least 40 mg, such as at least 60 mg or at least 80 mg of arabinogalactan per g of coffee solids. The arabinogalactan of the composition of the invention is preferably obtained by extraction of coffee beans.

2-Methylpropanal

The composition of the invention has a pleasant aroma and may have typical notes of coffee. 2-methylpropanal is a compound known for contributing a coffee-like aroma and the inventors have found that 2-methylpropanal is a good marker for this aroma characteristic of the product of the invention. In one embodiment, the composition of the invention comprises at least 10 microgram of 2-methylpropanal per gram of coffee solids, such as at least 15 microgram of 2-methylpropanal per gram of coffee solids.

Chlorogenic Acids

Chlorogenic acids are compounds with antioxidant activity. For the purpose of the present invention, the amount of chlorogenic acids is determined as the sum of the amounts of the chlorogenic acid homologues 3-caffeoylquinic acid (3-CQA), 4-caffeoylquinic acid (4-CQA), 5-caffeoylquinic acid (5-CQA), 3,4 dicaffeoylqunic acid (3,4-diCQA), 3,5-dicaffeoylquinic acid (3,5-diCQA), 4,5-dicaffeoylquinic acid (4,5-diCQA), 4-feruloylquinic acid (4-FQA), and 5-feruloylquinic acid (5-FQA). The chlorogenic acid isomers may be determined by HPLC with UV detection at 320 nm using 5-CQA as external standard to calculate the concentrations. In one embodiment the composition of the invention comprises at least 120 milligram of chlorogenic acids per gram of coffee solids, preferably at least 150 milligram or at least 200 milligram of chlorogenic acids per gram of coffee solids. The composition may e.g. comprise between 120 and 350 milligram of chlorogenic acids per gram of coffee solid, or between 200 and 300 milligram of chlorogenic acids per gram of coffee solid.

Food or Beverage Composition

A food or beverage composition according to the invention may be any food or beverage composition, including pet food composition, meant to be consumed by a human or animal, such as e.g. a beverage, e.g. a coffee beverage, a cocoa or chocolate beverage, a malted beverage, a fruit or juice beverage, a carbonated beverage, a soft drink, or a milk based beverage; a performance nutrition product, e.g. a performance nutrition bar, powder or ready-to-drink beverage; a medical nutrition product; a dairy product, e.g. a milk drink, a yogurt or other fermented dairy product; an ice cream product; a confectionary product, e.g. a chocolate product; a functional food or beverage, e.g. a slimming product, a fat burning product, a product for improving mental performance or preventing mental decline, or a skin improving product.

In a preferred embodiment a composition of the invention is a beverage. A beverage according to the invention may e.g. be in the form of a powder or liquid concentrate to be mixed with a suitable liquid, e.g. water or milk, before consumption, or a ready-to-drink beverage. By a ready-to-drink beverage is meant a beverage in liquid form ready to be consumed without further addition of liquid. A beverage according to the invention may comprise any other suitable ingredients known in the art for producing a beverage, such as e.g. sweeteners, e.g. sugar, such as invert sugar, sucrose, fructose, glucose, or any mixture thereof, natural or artificial sweetener; aromas and flavours, e.g. fruit, cola, coffee, or tea aroma and/or flavour; fruit or vegetable juice or puree; milk; stabilizers; emulsifiers; natural or artificial colour; preservatives; antioxidants, e.g. ascorbic acid; and the like. Any suitable acid or base may be used to achieve a desired pH of the product, e.g. citric acid or phosphoric acid. A beverage of the invention may be carbonated, carbon dioxide may be added by any suitable method known in the art. In a preferred embodiment a beverage comprises up to 10% sucrose or another sweetener in an amount yielding an equal degree of sweetness, more preferably between 2% and 5% sucrose or another sweetener in an amount yielding an equal degree of sweetness. The inventors have found that the refreshing and coffee-like character is best achieved if the level of sweetener is not too high. The optimal level of sweetener may depend on the amount of coffee solids, thus in a preferred embodiment the amount of sweetener is equal to or less than the amount giving a sweetness effect equal to a sucrose level (in percent by weight) of 5 times the amount of coffee solids (in percent by weight) plus 1. If the beverage is a liquid concentrate or a ready-to-drink beverage it may be subjected to a heat treatment to increase the shelf life or the product, e.g. by retorting, UHT (Ultra High Temperature) treatment, HTST (High Temperature Short Time) treatment, pasteurisation, or hot fill.

EXAMPLES

Example 1

A green coffee extract was prepared by extracting whole green coffee beans with water in a two-stage extraction process with a temperature in the first stage of 110° C. and in the second stage of 180° C., and drying the resulting extract by spray drying. 3 liquid beverage products, A1, A2 and A3, were prepared from this green coffee extract by mixing the ingredients in the table below.

|  | A1 | A2 | A3 |
|---|---|---|---|
| Green coffee extract, dry | 0.45% | 0.45% | 0.7% |
| Sugar | 3.0% | 3.0% | 5.0% |
| Fruit Flavor |  | 0.06% |  |
| Water | 96.55% | 96.49% | 94.3% |

Example 2

A beverage, B, based on roasted coffee was prepared by substituting the green coffee extract of the recipe of product A1 of example 1 with a water extract of roasted coffee (NESCAFE®). 129 panellists tasted product A1 and B and were asked to rate how refreshing each beverage was on a 7 point scale. Product A1 was given an average score of 3.2, whereas product B scored 2.8 on average. When asked which product was most refreshing, 66% of panellists found product A1 most refreshing.

Example 3

Beverages C and D were prepared by substituting the green coffee extract of the recipe of product A1 of example 1 with commercial green coffee extracts. For product C SVETOL® (Naturex SA, France) was used, for product D a green coffee extract from Oryza Oil and Fat chemical Co., Ltd., Japan ("Oryza") was used. 14 panellists evaluated products A1, B, C, D as well as 4 commercial beverages containing coffee extract (Aqua Ligne Café Minceur à boir (Laboratoires Vitarmonyl), Gayelord Hauser Minceur (Gayelord Hauser, France), CELLI FLORE® Stick Minceur (Laboratoires Juva Santé, France), and XLS Draineur Purifieur (Omega Pharma NV, Belgium)). The products were sorted and grouped based on sensory attributes by principal component analysis. Product A1 was described by the attributes "Coffee" and "Roasty" and grouped with product B and the commercial product Celli Flore Stick Minceur. Products C and D were grouped together and described by the attributes "Fruity" and "Warm brown spice". The commercial products Aqua Ligne Minceur à boir and Gayelord Hauser Minceur were grouped together and primarily described as "Fruity". Commercial product XLS was grouped by itself and primarily described by the attribute "Cooling". Based on the ingredients list and chemical analysis it was estimated that all the commercial products contained at most 0.14% green coffee solids.

Products A1, B, C, D were analysed for content of 2-methylpropanal before and after a heat treatment at 121° C. for 5 minutes. Results are shown in the table below in microgram per gram of coffee solids.

|  | A1 | B | C | D |
|---|---|---|---|---|
| 2-methylpropanal before heat treatment | 17.31 | 23.42 | 6.71 | 7.45 |
| 2-methylpropanal after heat treatment | 21.95 | 20.87 | 7.26 | 9.80 |

Example 4

Two batches of a dry green coffee extract produced as in example 1, and the two commercial green coffee extracts were analysed for some compositional parameters. The amount of chlorogenic acids was determined as the sum of the amounts of the chlorogenic acid isomers 3-caffeoylquinic acid (3-CQA), 4-caffeoylquinic acid (4-CQA), 5-caffeoylquinic acid (5-CQA), 3,4 dicaffeoylqunic acid (3,4-diCQA), 3,5-dicaffeoylquinic acid (3,5-diCQA), 4,5-dicaffeoylquinic acid (4,5-diCQA), 4-feruloylquinic acid (4-FQA), and 5-feruloylquinic acid (5-FQA). The chlorogenic acid isomers were determined by HPLC on a Spherisorb ODS1 column using a water/acetonitrile/phosphate gradient with UV detection at 320 nm using 5-CQA as external standard to calculate the concentrations. The arabinogalactan content was expressed as the sum of total arabinose and galactose determined by anion exchange chromatography (AEC) The total amount of arabinose and galactose, respectively, was determined as the sum the free sugar analysed by AEC before and after hydrolysis of the polysaccharide (expressed as anyhdrosugar). Results are shown in the table below, all values given as percent by weight.

|  | Example 1 Batch 1 | Example 1 Batch 2 | "Oryza" | SVETOL ® |
|---|---|---|---|---|
| Water | 3.29 | 3.04 | 2.31 | 3.32 |
| Total amino acids | 8.42 | n.d. | 3.39 | 3.84 |
| Total carbohydrates | 27.09 | 37.71 | 20.37 | 20.43 |
| Arabinogalactans | 13.12 | 19.93 | 0.48 | 0.68 |
| Chlorogenic acids | 24.03 | 17.91 | 54.98 | 38.15 | n.d.: not determined

The invention claimed is:
1. A food or beverage composition comprising 0.2 wt. % to 20 wt. % of green coffee solids and at least 20 mg of arabinogalactans per gram of green coffee solids, wherein at least 80 wt. % of said green coffee solids are water soluble, at least 10 mg of 2-methylpropanyl per gram of green coffee solids are present, said green coffee solids comprising between 120 and 350 mg of chlorogenic acids per gram of green coffee solids and at least 92 wt. % of said green coffee solids in the total composition are unroasted green coffee solids.

* * * * *